United States Patent
Furukawa (10) Patent No.: US 10,508,999 B2
(45) Date of Patent: Dec. 17, 2019

(54) SAMPLE HOLDER

(71) Applicant: Shimadzu Corporation, Kyoto (JP)

(72) Inventor: Hiroaki Furukawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 113 days.

(21) Appl. No.: 15/926,079

(22) Filed: Mar. 20, 2018

(65) Prior Publication Data

US 2019/0064085 A1 Feb. 28, 2019

(30) Foreign Application Priority Data

Aug. 23, 2017 (JP) ................. 2017-160497

(51) Int. Cl.
| | |
|---|---|
| G02B 21/34 | (2006.01) |
| H01J 49/04 | (2006.01) |
| C12M 1/16 | (2006.01) |
| C12M 1/20 | (2006.01) |
| G01N 23/2204 | (2018.01) |
| G01N 23/223 | (2006.01) |
| B01L 3/00 | (2006.01) |

(52) U.S. Cl.
CPC ........ *G01N 23/2204* (2013.01); *B01L 3/5055* (2013.01); *G01N 23/223* (2013.01)

(58) Field of Classification Search
CPC .............. B01L 3/5055; B01L 2300/43; B01L 2300/0609; B01L 3/505; G01N 23/223; G01N 23/2204; G01N 1/312; G01N 2021/0389; G01N 21/0303; G01N 1/31; G01N 2001/2833; G01N 2021/0364; G01N 21/8422; H01J 49/0409; H01J 49/0459

USPC ........ 356/244, 440, 246; 436/165; 378/208, 378/68; 422/401, 404, 409, 551, 563; 250/576; 73/864.91
See application file for complete search history.

(56) References Cited

U.S. PATENT DOCUMENTS

| | | | | |
|---|---|---|---|---|
| 5,657,383 | A * | 8/1997 | Gerber .................... | H04M 3/48 379/210.01 |
| 2006/0051251 | A1* | 3/2006 | Desrosiers ............ | B01L 3/5085 422/534 |
| 2006/0246598 | A1* | 11/2006 | Dai ....................... | B01L 3/5023 436/169 |
| 2010/0182599 | A1* | 7/2010 | Albin ....................... | G01J 3/02 356/326 |
| 2014/0011289 | A1* | 1/2014 | Smith ...................... | B01L 7/00 436/176 |
| 2014/0116160 | A1* | 5/2014 | St. Cyr ............... | H01J 49/0409 73/864.91 |

FOREIGN PATENT DOCUMENTS

| | | | |
|---|---|---|---|
| JP | 2016-176817 A | 10/2016 | |
| WO | WO-2018102467 A1 * | 6/2018 | ............... G01J 3/02 |

* cited by examiner

*Primary Examiner* — Kenneth J Malkowski
(74) *Attorney, Agent, or Firm* — Maier & Maier, PLLC (57) ABSTRACT

When conducting an analysis of a sample using an X-ray fluorescence spectrometer, a user allows a sample holder to hold the sample such that the sample is sandwiched between a first film and a second film, and mounts the sample holder in this state to the spectrometer. When conducting an analysis of the sample using a Fourier transform infrared spectrometer, the user allows the sample holder to hold the sample such that the sample is not sandwiched between the first film and the second film, and mounts the sample holder in this state to the spectrometer.

8 Claims, 7 Drawing Sheets

SAMPLE HOLDER

FIELD

The present invention relates to a sample holder that can be used in common by an X-ray fluorescence spectrometer and a Fourier transform infrared spectrometer and holds a sample to be analyzed.

BACKGROUND

Conventionally, Fourier transform infrared spectrometers (FT-IR) and X-ray fluorescence spectrometers (EDX) have been used as devices for analyzing foreign matters included in a sample (for example, see JP-A-2016-176817).

A Fourier transform infrared spectrometer is used for analyzing organic substances in a sample. The Fourier transform infrared spectrometer irradiates the sample with infrared light and detects reflection light from the sample by a detector. The Fourier transform infrared spectrometer creates a spectrum by performing a Fourier transform on an interferogram (detection signal) based on the reflection light. Organic substances included in the sample are analyzed on the basis of this spectrum.

An X-ray fluorescence spectrometer is used to analyze inorganic substances in a sample. The X-ray fluorescence spectrometer irradiates the sample with excited X-rays. The sample excited by excited X-rays emits fluorescence X-rays, and the emitted fluorescence X-rays are detected by a detector. The X-ray fluorescence spectrometer creates a spectrum on the basis of the detection signal from the detector. Inorganic substances included in the sample are then analyzed on the basis of this spectrum.

As described above, to analyze organic substances in a sample, the sample is mounted to a Fourier transform infrared spectrometer, and to analyze inorganic substances in the sample, the sample is mounted to an X-ray fluorescence spectrometer.

SUMMARY

In a sample analysis with an X-ray fluorescence spectrometer and a Fourier transform infrared spectrometer as described above, there is a problem such that a user's job involved in mounting a sample becomes complicated.

Specifically, to conduct an analysis of a sample using the X-ray fluorescence spectrometer, a user places the sample into a special sample container and mounts this sample container to a sample mounting portion. On the other hand, to conduct an analysis of a sample using the Fourier transform infrared spectrometer, the user directly mounts the sample to a sample mounting portion with tweezers, for example. Therefore, the user needs to take out the sample from the sample container and directly mount the sample to the sample mounting portion, or to put the sample which has been mounted to the sample mounting portion into a sample container, which entails a problem of a user's job being complicated. Particularly when a sample to be analyzed is small, the user needs to do the job with great care to prevent loss of the sample during the movement of the sample, which leads to a problem of an increase in work burden of the user.

The present invention is accomplished in view of the above circumstances, and aims to provide a sample holder capable of simplifying a user's job involved in mounting a sample in conducting an analysis of the sample with an X-ray fluorescence spectrometer and a Fourier transform infrared spectrometer.

(1) The sample holder according to the present invention is a sample holder that can be used in common by an X-ray fluorescence spectrometer and a Fourier transform infrared spectrometer and holds a sample to be analyzed. The sample holder includes a holder body and a pair of films. The pair of films is attached to the holder body. During an analysis of the sample with the X-ray fluorescence spectrometer, the sample is irradiated with X-rays through one of the pair of films while being sandwiched between the pair of films. During an analysis of the sample with the Fourier transform infrared spectrometer, the sample is irradiated with infrared rays not through the pair of films while not being sandwiched between the pair of films.

According to this configuration, when conducting the analysis of the sample using the X-ray fluorescence spectrometer, a user allows the sample holder to hold the sample such that the sample is sandwiched between the pair of films, and mounts the sample holder in this state to the spectrometer. When conducting the analysis of the sample using the Fourier transform infrared spectrometer, the user allows the sample holder to hold the sample such that the sample is not sandwiched between the pair of films, and mounts the sample holder in this state to the spectrometer.

Therefore, the user can conduct the analysis of the sample only by mounting the sample holder holding the sample to the respective spectrometers without taking out the sample from the sample holder.

Accordingly, a user's job involved in mounting the sample in conducting the analysis of the sample with the X-ray fluorescence spectrometer and the Fourier transform infrared spectrometer can be simplified.

(2) The other of the pair of films may be provided with an adhesive layer on a surface facing the one of the pair of films in a state where the sample is sandwiched between the pair of films.

According to this configuration, when the user puts the sample into contact with the adhesive layer, the sample can be held by adhesive force of the adhesive layer.

Therefore, the sample can be held by the sample holder with a simple structure.

(3) The holder body may include a pair of main body plates. Each of the pair of main body plates is formed into a plate shape. The one of the pair of films may be attached to one of the pair of main body plates, and the other of the pair of films may be attached to the other of the pair of main body plates.

According to this configuration, the respective films can be kept in a stable state in the sample holder.

(4) The holder body may be configured to sandwich the sample between the pair of films when being folded such that the pair of main body plates faces each other.

According to this configuration, the sample can be sandwiched between the pair of films by simply folding the pair of main body plates.

(5) The pair of main body plates may have openings to which the pair of films is attached, respectively. Each of the pair of films may be transparent.

According to this configuration, the user can visually identify the sample held by the sample holder through the openings.

Thus, when mounting the sample holder holding the sample to the spectrometer, the user can mount the sample holder while visually checking the sample, thereby being capable of placing the sample at a position suitable for analysis.

(6) The one of the pair of films may be attached to the one of the pair of main body plates on a surface which is to be an outer surface when the sample is sandwiched between the pair of films. The other of the pair of films may be attached to the other of the pair of main body plates on a surface which is to be an inner surface when the sample is sandwiched between the pair of films.

According to this configuration, the one of the pair of films is attached to the one of the pair of main body plates on a surface which is to be an outer surface when the sample is sandwiched between the pair of films.

Therefore, when conducting the analysis of the sample using the X-ray fluorescence spectrometer, the user can mount the sample holder in such a way as to bring the sample as close to the spectrometer as possible.

Accordingly, during the analysis of the sample with the X-ray fluorescence spectrometer, the sample can be accurately irradiated with fluorescence X-rays.

Thus, analysis accuracy in the analysis of the sample with the X-ray fluorescence spectrometer can be improved.

In addition, the other of the pair of films is attached to the other of the pair of main body plate on a surface which is to be an inner surface when the sample is sandwiched between the pair of films.

Therefore, the distance between one of the pair of films and the other of the pair of films can be decreased in a state where the sample is sandwiched between the pair of films.

Thus, the sample can be stably held between the pair of films.

(7) The pair of films may be made of a same material.

According to this configuration, an increase in complexity of peak shapes in spectra acquired by the respective spectrometers can be prevented.

(8) The holder body may be provided with a mark indicating an orientation of mounting of the holder body on an opposite surface from a side irradiated with X-rays during the analysis of the sample with the X-ray fluorescence spectrometer, and on an opposite surface from a side irradiated with infrared rays during the analysis of the sample with the Fourier transform infrared spectrometer.

According to this configuration, when mounting the sample holder to the respective spectrometers, the user can mount the sample holder in the correct orientation.

According to the present invention, when conducting the analysis of the sample using the X-ray fluorescence spectrometer, the user allows the sample holder to hold the sample such that the sample is sandwiched between the pair of films, and mounts the sample holder with this state to the spectrometer. When conducting the analysis of the sample using the Fourier transform infrared spectrometer, the user allows the sample holder to hold the sample such that the sample is not sandwiched between the pair of films, and mounts the sample holder with this state to the spectrometer. Therefore, the user can conduct the analysis of the sample only by mounting the sample holder holding the sample to the respective spectrometers without taking out the sample from the sample holder. Accordingly, a user's job involved in mounting the sample in conducting the analysis of the sample with the X-ray fluorescence spectrometer and the Fourier transform infrared spectrometer can be simplified.

DETAILED DESCRIPTION

1. Configuration of Analysis System

Figure 1:
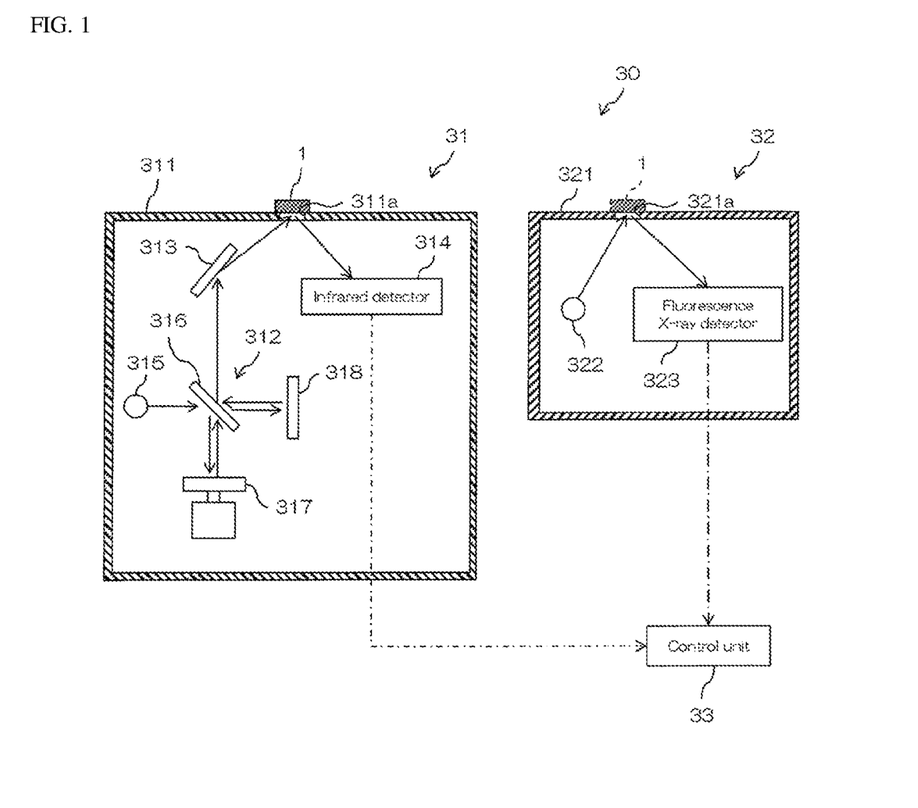
FIG. 1 is a schematic view illustrating an example of a configuration of an analysis system where a sample holder according to one embodiment of the present invention is mounted.

FIG. 1 is a schematic view illustrating an example of a configuration of an analysis system 30 where a sample holder 1 according to one embodiment of the present invention is mounted.

The analysis system 30 is for analyzing organic substances and inorganic substances included in a sample (sample including foreign matters), and includes a Fourier transform infrared spectrometer 31, an X-ray fluorescence spectrometer 32, and a control unit 33.

The Fourier transform infrared spectrometer 31 includes a housing 311, an interferometer 312, a reflecting mirror 313, and an infrared detector 314.

The housing 311 is formed into a box shape. Inside the housing 311, the interferometer 312, the reflecting mirror 313, and the infrared detector 314 are disposed. An upper surface of the housing 311 serves as a mounting portion where the sample (sample holder 1) is mounted. An opening 311a is formed in the upper surface of the housing 311.

The interferometer 312 is for generating interfering light, and includes a light source 315, a half mirror 316, a moving mirror 317, and a fixed mirror 318.

The light source 315 emits infrared light (infrared ray) as measurement light.

The half mirror 316 is disposed away from the light source 315. The half mirror 316 is capable of reflecting a portion of incoming light and transmitting the rest of the incoming light.

The moving mirror 317 is disposed away from the half mirror 316. The moving mirror 317 is configured to be movable along a direction in which the moving mirror 317 faces the half mirror 316. The moving mirror 317 moves along the direction in which the moving mirror 317 faces the half mirror 316 when a driving force is applied thereto from a drive source such as a motor.

The fixed mirror 318 is disposed on the opposite side of the light source 315 with the half mirror 316 interposed therebetween.

The reflecting mirror 313 is disposed away from the opening 311a in the housing 311.

The infrared detector 314 is disposed away from the opening 311a in the housing 311 and the reflecting mirror 313. The infrared detector 314 is an MCT (HgCdTe) detector, for example. The infrared detector 314 is configured to detect incoming infrared light and acquire a detection signal according to the detected infrared light. Specifically, the infrared detector 314 is configured to acquire an interferogram according to infrared light.

When the Fourier transform infrared spectrometer 31 is used, the sample holder 1 holding the sample is firstly mounted on the upper surface of the housing 311 by a user. Specifically, the sample holder 1 is mounted on the upper surface of the housing 311 so as to cover the opening 311a. With this state, infrared light is emitted from the light source 315. The infrared light from the light source 315 reaches the half mirror 316.

A portion of the infrared light reaching the half mirror 316 passes through the half mirror 316 to reach the fixed mirror 318, and the rest is reflected by the half mirror 316 and reaches the moving mirror 317. At that time, the moving mirror 317 moves along the direction in which the moving mirror 317 faces the half mirror 316 due to the driving force applied thereto.

The infrared light reflected by the fixed mirror 318 is reflected by the half mirror 316 and travels toward the reflecting mirror 313. The infrared light reflected by the moving mirror 317 passes through the half mirror 316 and travels toward the reflecting mirror 313. Thus, the infrared light reflected by the fixed mirror 318 and the infrared light reflected by the moving mirror 317 are combined to become infrared interfering light, and travel toward the reflecting mirror 313. The combined infrared light is then reflected by the reflecting mirror 313 and passes through the opening 311a to be delivered to the sample holder 1 (sample held by the sample holder 1). Then, reflection light from the sample holder 1 (sample held by the sample holder 1) enters the infrared detector 314.

The infrared detector 314 outputs an interferogram according to the incident infrared light as a detection signal. The control unit 33 performs a Fourier transform on the interferogram outputted from the infrared detector 314, thereby acquiring spectrum intensity distribution data.

On the other hand, the X-ray fluorescence spectrometer 32 includes a housing 321, a light source 322, and a fluorescence X-ray detector 323.

The housing 321 is formed into a box shape. Inside the housing 321, the light source 322 and the fluorescence X-ray detector 323 are disposed. An upper surface of the housing 321 serves as a mounting portion where the sample (sample holder 1) is mounted. An opening 321a is formed in the upper surface of the housing 321.

The light source 322 is disposed away from the opening 321a in the housing 321. The light source 322 emits excited X-rays as measurement light.

The fluorescence X-ray detector 323 is configured to detect incoming X-rays (fluorescence X-rays) and acquire a detection signal according to the detected light.

When the X-ray fluorescence spectrometer 32 is used, the sample holder 1 holding the sample is firstly mounted on the upper surface of the housing 321 by the user. Specifically, the sample holder 1 is mounted on the upper surface of the housing 321 so as to cover the opening 321a. With this state, excited X-rays are emitted from the light source 322. When the sample holder 1 (sample held by the sample holder 1) is irradiated with the excited X-rays, fluorescence X-rays are radiated from the sample excited by the excited X-rays. The fluorescence X-rays from the sample are then detected by the fluorescence X-ray detector 323.

The control unit 33 acquires spectrum intensity distribution data on the basis of the detection signal from the fluorescence X-ray detector 323.

The control unit 33 analyzes organic substances and inorganic substances included in the sample on the basis of the spectrum data acquired as described above. Specifically, the control unit 33 analyzes organic substances included in the sample on the basis of the spectrum data obtained from the detection signal from the infrared detector 314. The control unit 33 also analyzes inorganic substances included in the sample on the basis of the spectrum data obtained from the detection signal from the fluorescence X-ray detector 323.

When conducting an analysis of the sample with the analysis system 30 as described above, the user needs to mount the sample to the Fourier transform infrared spectrometer 31 and the X-ray fluorescence spectrometer 32, respectively. The sample holder 1 is configured as described below in order to prevent the user's job from being complicated in this case.

2. Configuration of Sample Holder

Figure 2:
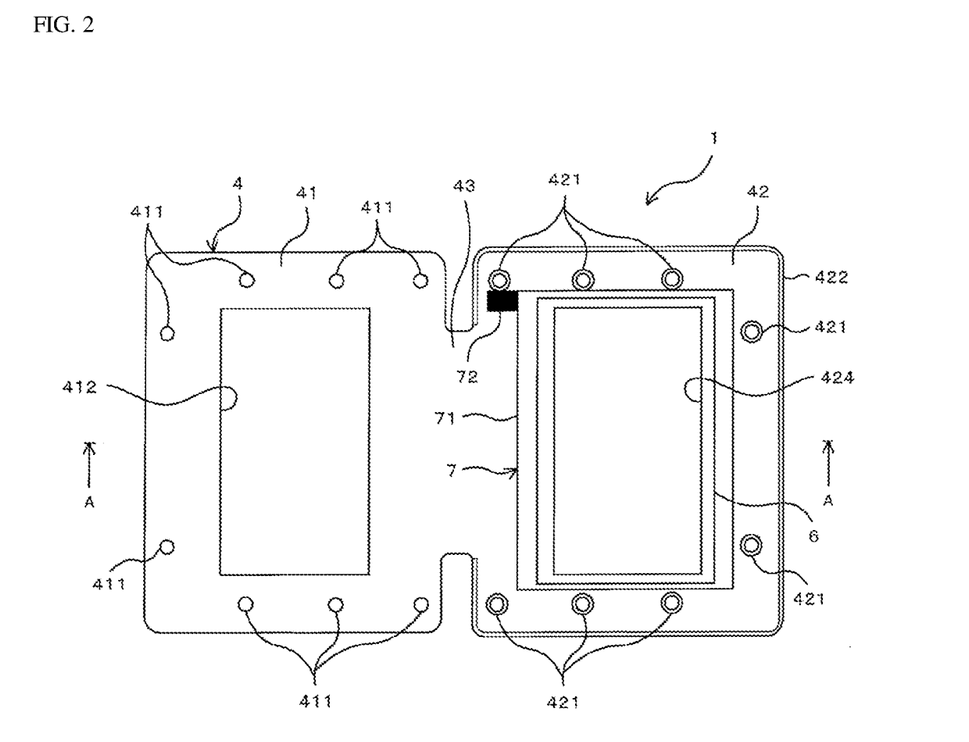
FIG. 2 is a plan view illustrating a state where the sample holder in an open state is viewed from an inner surface.
Figure 3:
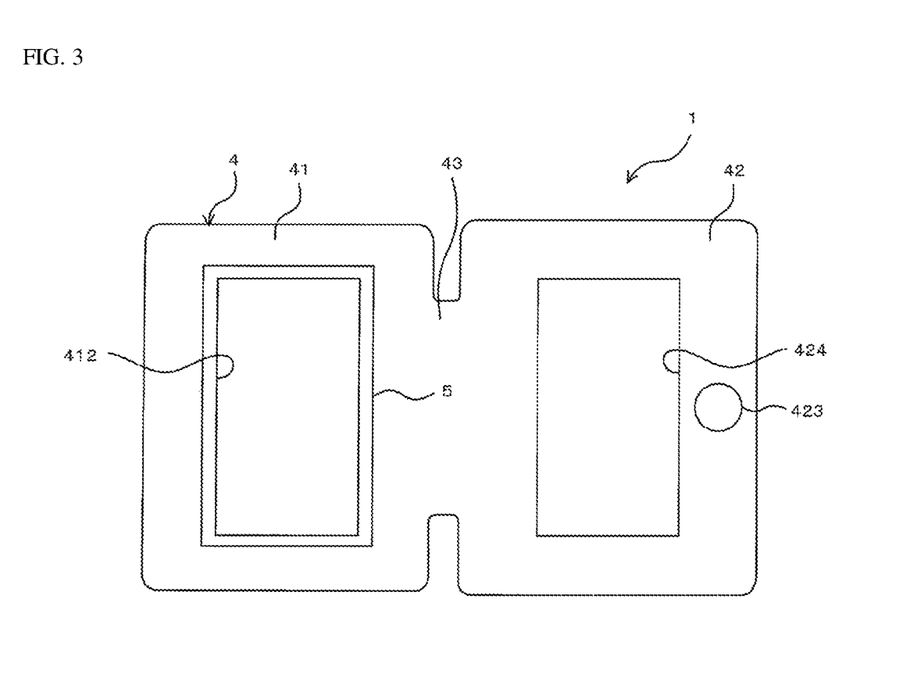
FIG. 3 is a plan view illustrating a state where the sample holder in an open state is viewed from an outer surface.
Figure 4:
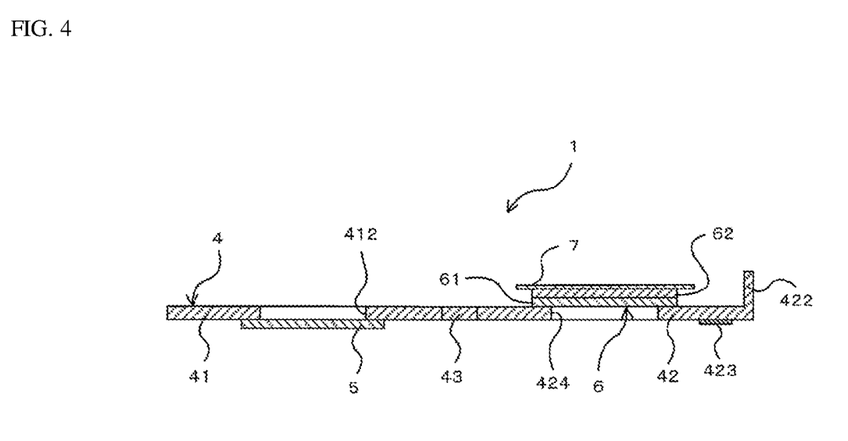
FIG. 4 is a sectional view along a line A-A in FIG. 2.

FIG. 2 is a plan view illustrating a state where the sample holder 1 in an open state is viewed from an inner surface. FIG. 3 is a plan view illustrating a state where the sample holder 1 in an open state is viewed from an outer surface. FIG. 4 is a sectional view along a line A-A in FIG. 2.

The sample holder 1 is a member for holding a sample to be analyzed and is foldable. The sample holder 1 includes a holder body 4, a first film 5, a second film 6, and a third film 7. In FIGS. 2 to 4, the sample holder 1 in an open state is illustrated.

The holder body 4 is formed into a flat plate which is foldable. The holder body 4 is made of a resin material such as plastic or paper. The holder body 4 includes a first main body plate 41, a second main body plate 42, and a folded part 43. A surface which is to be an inner surface when the holder body 4 is folded is defined as an inner surface (inner surfaces of the first main body plate 41, the second main body plate 42, and the folded part 43) of the holder body 4, and a surface which is to be an outer surface when the holder body 4 is folded is defined as an outer surface (outer surfaces of the first main body plate 41, the second main body plate 42, and the folded part 43) of the holder body 4.

The first main body plate 41 is formed into a rectangular flat shape in a plan view. The first main body plate 41 is formed with a plurality of protrusions 411. The first main body plate 41 is formed with a first opening 412. The first main body plate 41 is one example of one of the pair of main body plates.

The plurality of protrusions 411 is provided on the peripheral edge of the inner surface of the first main body plate 41. The protrusions 411 are spaced. Each of the protrusions 411 is circular in a plan view and protrudes from the inner surface of the first main body plate 41 in a direction (perpendicular direction) perpendicular to the inner surface of the first main body plate 41.

The first opening 412 is formed into a rectangular shape in a plan view and extends through a central part of the first main body plate 41 in the perpendicular direction.

The second main body plate 42 is located away from the first main body plate 41. The second main body plate 42 is formed into a rectangular flat shape in a plan view. The outer shape of the second main body plate 42 is slightly larger than the outer shape of the first main body plate 41. The second main body plate 42 is provided with a plurality of engagement sections 421, a protruding wall 422, and a mark 423. The second main body plate 42 is formed with a second opening 424. The second main body plate 42 is one example of the other of the pair of main body plates. The first main body plate 41 and the second main body plate 42 constitute a pair of main body plates.

The plurality of engagement sections 421 is provided on the peripheral edge of the inner surface of the second main body plate 42. The engagement sections 421 are spaced.

Each of the engagement sections 421 is torus in a plan view and protrudes in the perpendicular direction from the inner surface of the second main body plate 42. Positions where the engagement sections 421 are formed on the inner surface of the second main body plate 42 correspond to positions where the protrusions 411 are formed on the inner surface of the first main body plate 41.

The protruding wall 422 protrudes in the perpendicular direction from the outer edge of the inner surface of the second main body plate 42.

As illustrated in FIGS. 3 and 4, the mark 423 is formed on the peripheral edge of the outer surface of the second main body plate 42. The mark 423 is formed into a circular shape in a plan view. As described later, the mark 423 is provided on the opposite surface from the side irradiated with X-rays during an analysis of a sample using the Fourier transform infrared spectrometer 31. Further, the mark 423 is provided on the opposite surface from the side irradiated with infrared light (infrared ray) during an analysis of a sample using the X-ray fluorescence spectrometer 32.

The second opening 424 is formed into a rectangular shape in a plan view and extends through a central part of the second main body plate 42 in the perpendicular direction. The second opening 424 in the second main body plate 42 and the first opening 412 in the first main body plate 41 are one example of an opening.

The folded part 43 is located between the first main body plate 41 and the second main body plate 42. The folded part 43 is formed into a narrow rectangular shape and has flexibility. One end of the folded part 43 is connected to the first main body plate 41, and the other end of the folded part 43 is connected to the second main body plate 42.

The first film 5 is formed into a rectangular sheet shape in a plan view and attached to the first main body plate 41. Specifically, the first film 5 is attached to the outer surface of the first main body plate 41 so as to cover the first opening 412. That is, the first opening 412 is covered by the first film 5. The first film 5 is made of a resin material, such as polyethylene, polypropylene, or polycarbonate, and is transparent. The thickness of the first film 5 is 5 μm, for example. The first film 5 is one example of one of the pair of films.

The second film 6 is formed into a rectangular sheet shape in a plan view and attached to the second main body plate 42. Specifically, the second film 6 is attached to the inner surface of the second main body plate 42 so as to cover the second opening 424. That is, the second opening 424 is covered by the second film 6. The second film 6 has a laminate structure including a base layer 61 and an adhesive layer 62. That is, the second film 6 has a two-layer structure. The second film 6 is one example of the other of the pair of films. The first film 5 and the second film 6 constitute a pair of films.

The base layer 61 is in close contact with (attached to) the second main body plate 42. That is, the base layer 61 is located on one side (lower side in FIG. 4) of the second film 6 in the thickness direction. The base layer 61 is made of a material same as the material of the first film 5.

The adhesive layer 62 is provided on the base layer 61. Specifically, the adhesive layer 62 is provided on a surface of the base layer 61 on the other side (upper side in FIG. 4) in the thickness direction with a constant thickness. The adhesive layer 62 has adhesion and is made of a material not including an inorganic element.

Thus, the second film 6 is composed of two layers which are the base layer 61 and the adhesive layer 62, and the thickness thereof is 50 μm or less, for example.

The third film 7 is attached to the adhesive layer 62. Specifically, the third film 7 is attached to the surface of the adhesive layer 62 on the other side (upper side in FIG. 4) in the thickness direction. The third film 7 is a release film and includes a main body 71 and a projection 72. The main body 71 is formed into a rectangular sheet shape in a plan view. As illustrated in FIG. 2, the projection 72 projects from an end of the main body 71 in the horizontal direction.

3. Way of Allowing Sample Holder to Hold Sample and Mounting Sample Holder

Figure 5A:
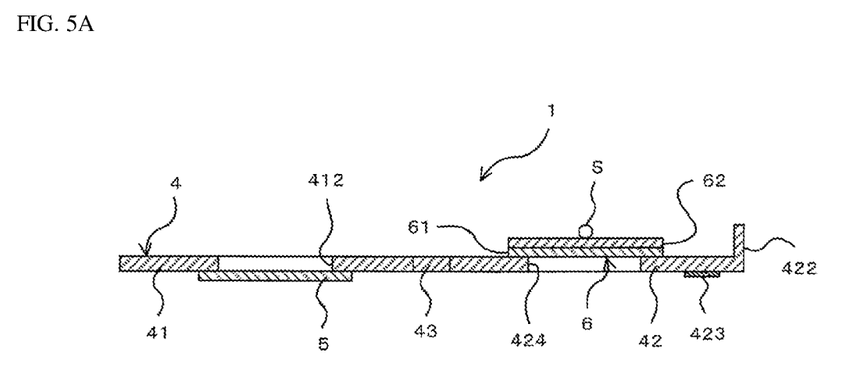
FIG. 5A is a sectional view illustrating a state where a sample is held by an adhesive layer of the sample holder.
Figure 5B:
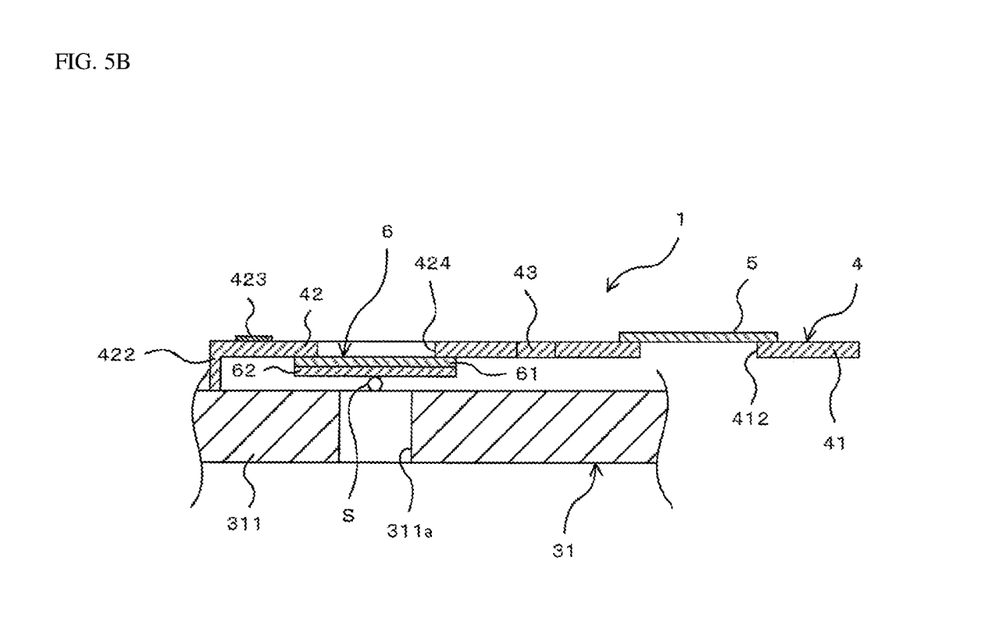
FIG. 5B is a sectional view illustrating a state where the sample holder is mounted to a Fourier transform infrared spectrometer.
Figure 5C:
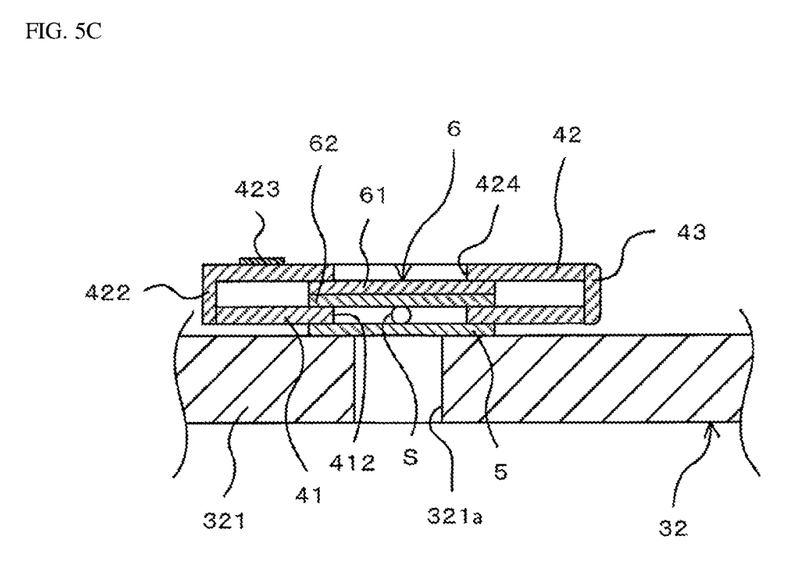
FIG. 5C is a sectional view illustrating a state where the sample holder is mounted to an X-ray fluorescence spectrometer.

Now, a way of allowing the sample holder 1 to hold the sample S and mounting the sample holder 1 will be described below with reference to FIG. 4 and FIGS. 5A to 5C. FIG. 5A is a sectional view illustrating a state where the sample S is held by the adhesive layer 62 of the sample holder 1. FIG. 5B is a sectional view illustrating a state where the sample holder 1 is mounted to the Fourier transform infrared spectrometer 31. FIG. 5C is a sectional view illustrating a state where the sample holder 1 is mounted to the X-ray fluorescence spectrometer 32.

To allow the sample holder 1 to hold the sample S, the user firstly opens the sample holder 1 so that the inner surface thereof is directed upward as illustrated in FIG. 4. Even if the sample S is placed on the second film 6 with this state, the sample S is not held because of the third film 7 being attached to the adhesive layer 62.

In this state, the user pulls the projection 72 (see FIG. 2) of the third film 7 to peel the third film 7 from the second film 6. Thus, the adhesive layer 62 of the second film 6 is exposed.

Then, the user places the sample S on the exposed adhesive layer 62. Thus, as illustrated in FIG. 5A, the sample S is held by the adhesive layer 62 by adhesive force of the adhesive layer 62.

With the sample S being held by the sample holder 1 as described above, the user mounts the sample holder 1 to the Fourier transform infrared spectrometer 31 as illustrated in FIG. 5B. Specifically, the sample holder 1 which remains open is mounted to the Fourier transform infrared spectrometer 31 such that the inner surface is directed downward and the sample S held by the adhesive layer 62 faces the opening 311a.

In this case, the user can visually identify the mark 423 as viewed from above the sample holder 1, thereby recognizing that the orientation of the sample holder 1 is correct. The user also mounts the sample holder 1 to the Fourier transform infrared spectrometer 31 on a location where the sample S overlaps the opening 311a, while visually identifying the sample S from above the sample holder 1 through the second film 6. Specifically, when mounting the sample holder 1 to the Fourier transform infrared spectrometer 31, the user visually identifies the sample S through the transparent second film 6 to align the sample holder 1.

The sample holder 1 mounted to the Fourier transform infrared spectrometer 31 is pressed by an unillustrated holding member from above to be fixed on the Fourier transform infrared spectrometer 31. As described above, in the case where the sample holder 1 is mounted to the Fourier transform infrared spectrometer 31, the sample S is not sandwiched between the first film 5 and the second film 6.

With this state, infrared light is emitted toward the sample S held by the sample holder 1.

The user also extracts the sample holder 1 from the Fourier transform infrared spectrometer 31 and folds the sample holder 1. Specifically, the user moves the first main body plate 41 and the second main body plate 42 close to each other such that the first main body plate 41 and the second main body plate 42 face each other. Thus, the folded part 43 is bent, which allows the protrusions 411 on the first main body plate 41 to be engaged with the engagement sections 421 on the second main body plate 42. Further, the protruding wall 422 of the second main body plate 42 comes into contact with the outer edge of the first main body plate 41. Thus, the sample S is sandwiched between the first film 5 and the second film 6.

With the sample holder 1 being folded as described above, the user mounts the sample holder 1 to the X-ray fluorescence spectrometer 32 as illustrated in FIG. 5C. Specifically, the sample holder 1 is mounted to the X-ray fluorescence spectrometer 32 in a folded (closed) state with the first main body plate 41 facing downward.

In this case, the user can visually identify the mark 423 as viewed from above the sample holder 1, thereby recognizing that the orientation of the sample holder 1 is correct. The user also mounts the sample holder 1 to the X-ray fluorescence spectrometer 32 on a location where the sample S overlaps the opening 321a, while visually identifying the sample S from above the sample holder 1 through the first film 5 and the second film 6. Specifically, when mounting the sample holder 1 to the X-ray fluorescence spectrometer 32, the user visually identifies the sample S through the first film 5 and the second film 6, which are transparent, to align the sample holder 1.

With this state, excited X-rays are emitted toward the sample S held by the sample holder 1.

In the analysis system 30, the control unit 33 analyzes organic substances included in the sample S on the basis of spectrum data obtained from the detection signal from the infrared detector 314. The control unit 33 also analyzes inorganic substances included in the sample S on the basis of the spectrum data obtained from the detection signal from the fluorescence X-ray detector 323.

During the analysis of the organic substances included in the sample S, the control unit 33 also uses the spectrum data obtained from the detection signal from the fluorescence X-ray detector 323, in addition to the spectrum data obtained from the detection signal from the infrared detector 314. Specifically, a peak of X-rays due to the Compton scattering and a peak of X-rays due to the Rayleigh scattering appear in the spectrum data obtained from the detection signal from the fluorescence X-ray detector 323. The control unit 33 analyzes organic substances in the sample S on the basis of these peaks as well as the spectrum data obtained from the detection signal from the infrared detector 314.

As described above, the first film 5 and the base layer 61 are made of the same material. This can prevent an increase in complexity of the shape of the peak of X-rays due to the Compton scattering and the shape of the peak of X-rays due to the Rayleigh scattering which appear in the spectrum data obtained from the detection signal from the fluorescence X-ray detector 323. Therefore, the organic substances in the sample S can be accurately analyzed.

After the sample S is analyzed in this way, the sample holder 1 is kept in a predetermined storage space in a folded (closed) state to hold the sample S. If a plurality of sample holders 1 is kept upright (along the vertical direction), for example, the storage space can be reduced.

4. Operation and Effects (1) According to the present embodiment, when conducting an analysis of the sample S using the X-ray fluorescence spectrometer 32, the user allows the sample holder 1 to hold the sample S such that the sample S is sandwiched between the first film 5 and the second film 6, and mounts the sample holder 1 in this state to the spectrometer 32, as illustrated in FIG. 5C. When conducting an analysis of the sample S using the Fourier transform infrared spectrometer 31, the user allows the sample holder 1 to hold the sample S such that the sample S is not sandwiched between the first film 5 and the second film 6, and mounts the sample holder 1 in this state to the spectrometer 31, as illustrated in FIG. 5B.

Therefore, the user can conduct the analysis of the sample S only by mounting the sample holder 1 holding the sample S to the respective spectrometers without taking out the sample S from the sample holder 1.

Accordingly, a user's job involved in mounting the sample S in conducting the analysis of the sample S with the Fourier transform infrared spectrometer 31 and the X-ray fluorescence spectrometer 32 can be simplified.

(2) According to the present embodiment, the second film 6 in the sample holder 1 includes the adhesive layer 62 as illustrated in FIG. 5C. The adhesive layer 62 is provided to the second film 6 on the side facing the first film 5 in a state where the sample S is sandwiched between the first film 5 and the second film 6.

Therefore, when the user puts the sample S into contact with the adhesive layer 62, the sample S can be held by adhesive force of the adhesive layer 62 as illustrated in FIG. 5A.

Thus, the sample S can be held by the sample holder 1 with a simple structure.

(3) According to the present embodiment, in the sample holder 1, the first film 5 is attached to the first main body plate 41 and the second film 6 is attached to the second main body plate 42 as illustrated in FIG. 4.

Therefore, the first film 5 and the second film 6 can be kept in a stable state, respectively, in the sample holder 1.

(4) According to the present embodiment, the holder body 4 is configured to sandwich the sample S between the first film 5 and the second film 6 when being folded such that the first main body plate 41 and the second main body plate 42 face each other, as illustrated in FIG. 5C.

Therefore, the sample S can be sandwiched between the first film 5 and the second film 6 by simply folding the first main body plate 41 and the second main body plate 42.

(5) According to the present embodiment, in the sample holder 1, the first opening 412 is formed in the first main body plate 41 and the second opening 424 is formed in the second main body plate 42, as illustrated in FIG. 4. The transparent first film 5 is attached to the first opening 412, and the transparent second film 6 is attached to the second opening 424.

When mounting the sample holder 1 to the Fourier transform infrared spectrometer 31, the user visually identifies the sample S through the transparent second film 6 to align the sample holder 1. When mounting the sample holder 1 to the X-ray fluorescence spectrometer 32, the user visually identifies the sample S through the first film 5 and the second film 6, which are transparent, to align the sample holder 1.

In this way, the user can visually identify the sample S held by the sample holder 1 through the first opening 412 and the second opening 424, respectively.

Thus, when mounting the sample holder 1 holding the sample S to the respective spectrometers, the user can mount the sample holder 1 while visually checking the sample S, thereby being capable of placing the sample S at a position suitable for analysis.

(6) According to the present embodiment, in the sample holder 1, the first film 5 is attached to an outer surface of the first main body plate 41 as illustrated in FIG. 4.

Therefore, when conducting an analysis of the sample S using the X-ray fluorescence spectrometer 32, the user can mount the sample holder 1 in such a way as to bring the sample S as close to the spectrometer as possible, as illustrated in FIG. 5C.

Accordingly, during the analysis of the sample S using the X-ray fluorescence spectrometer 32, the sample S can be accurately irradiated with fluorescence X-rays.

Thus, analysis accuracy in the analysis of the sample S with the X-ray fluorescence spectrometer 32 can be improved.

Further, in the sample holder 1, the second film 6 is attached to an inner surface of the second main body plate 42 as illustrated in FIG. 4.

Therefore, the distance between the first film 5 and the second film 6 can be decreased in a state where the sample S is sandwiched between the first film 5 and the second film 6, as illustrated in FIG. 5C.

Thus, the sample S can be stably held between the first film 5 and the second film 6.

(7) According to the present embodiment, in the sample holder 1, the first film 5 and the base layer 61 are made of the same material.

This can prevent an increase in complexity of the shape of the peak of X-rays due to the Compton scattering and the shape of the peak of X-rays due to the Rayleigh scattering which appear in the spectrum data obtained from the detection signal from the fluorescence X-ray detector 323.

Therefore, organic substances in the sample S can be accurately analyzed.

(8) According to the present embodiment, the mark 423 is provided on the opposite surface from the side irradiated with X-rays during an analysis of the sample S using the Fourier transform infrared spectrometer 31, as illustrated in FIG. 5B. Further, the mark 423 is provided on the opposite surface from the side irradiated with infrared light (infrared ray) during the analysis of the sample S using the X-ray fluorescence spectrometer 32, as illustrated in FIG. 5C.

Thus, when mounting the sample holder 1 to the respective spectrometers, the user can mount the sample holder 1 in the correct orientation.

5. Modifications

The above embodiment has described that the sample holder 1 is foldable such that the first main body plate 41 and the second main body plate 42 face each other. However, the configuration is not limited thereto, and any other configurations can be applied. For example, the sample holder 1 may be configured such that the first main body plate 41 and the second main body plate 42 slide while facing each other.

The above embodiment has described that the mark 423 is used in common for the case of using the Fourier transform infrared spectrometer 31 and the case of using the X-ray fluorescence spectrometer 32. However, different marks 423 may be provided for the case of using the Fourier transform infrared spectrometer 31 and the case of using the X-ray fluorescence spectrometer 32. Specifically, the sample holder 1 may be provided with a plurality of marks 423.

What is claimed is:

1. A sample holder that is used in common by an X-ray fluorescence spectrometer and a Fourier transform infrared spectrometer and holds a sample to be analyzed, the sample holder comprising:
a holder body; and
a pair of films attached to the holder body;
wherein,
when an analysis of a sample is conducted with the X-ray fluorescence spectrometer, the sample is irradiated with X-rays through one of the pair of films while being sandwiched between the pair of films, and
when an analysis of a sample is conducted with the Fourier transform infrared spectrometer, the sample is irradiated with infrared rays not through the pair of films while not being sandwiched between the pair of films.

2. The sample holder according to claim 1, wherein the other of the pair of films is provided with an adhesive layer on a surface facing the one of the pair of films in a state where a sample is sandwiched between the pair of films.

3. The sample holder according to claim 1, wherein the holder body includes a pair of main body plates, each of which is formed into a plate shape, and
the one of the pair of films is attached to one of the pair of main body plates and the other of the pair of films is attached to the other of the pair of main body plates.

4. The sample holder according to claim 3, wherein the holder body is configured to sandwich the sample between the pair of films when being folded such that the pair of main body plates faces each other.

5. The sample holder according to claim 3, wherein the pair of main body plates has openings to which the pair of films is to be attached, respectively, and
each of the pair of films is transparent.

6. The sample holder according to claim 3, wherein the one of the pair of films is attached to the one of the pair of main body plates on a surface which is to be an outer surface when the sample is sandwiched between the pair of films, and
the other of the pair of films is attached to the other of the pair of main body plates on a surface which is to be an inner surface when the sample is sandwiched between the pair of films.

7. The sample holder according to claim 1, wherein the pair of films is made of a same material.

8. The sample holder according to claim 1, wherein the holder body is provided with a mark indicating an orientation of mounting of the holder body on an opposite surface from a side irradiated with X-rays during the analysis of the sample with the X-ray fluorescence spectrometer, and on an opposite surface from a side irradiated with infrared rays during the analysis of the sample with the Fourier transform infrared spectrometer.

* * * * *